United States Patent
Pedrizzetti et al.

(10) Patent No.: US 8,098,912 B2
(45) Date of Patent: *Jan. 17, 2012

(54) METHOD OF TRACKING POSITION AND VELOCITY OF OBJECTS' BORDERS IN TWO OR THREE DIMENSIONAL DIGITAL IMAGES, PARTICULARLY IN ECHOGRAPHIC IMAGES

(75) Inventors: Gianni Pedrizzetti, Prato (IT); Giovanni Tonti, Sulmona (IT)

(73) Assignees: Esoate S.p.A., Milan (IT); Amid Srl, Sulmona (AQ) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/015,264

(22) Filed: Jan. 16, 2008

(65) Prior Publication Data
US 2008/0118109 A1    May 22, 2008

Related U.S. Application Data

(63) Continuation of application No. 10/956,797, filed on Sep. 30, 2004, now Pat. No. 7,343,031.

(30) Foreign Application Priority Data

Sep. 30, 2003  (EP) .................................... 03425639

(51) Int. Cl.
*G06K 9/00* (2006.01)
(52) U.S. Cl. ........ 382/128; 382/103; 382/107; 382/199; 367/87; 600/437
(58) Field of Classification Search .................. 382/103
See application file for complete search history.

(56) References Cited

U.S. PATENT DOCUMENTS

| | | | |
|---|---|---|---|
| 5,622,174 A * | 4/1997 | Yamazaki | 600/441 |
| 5,709,211 A | 1/1998 | Machida | |
| 2001/0055425 A1 * | 12/2001 | Chiu | 382/199 |
| 2002/0072674 A1 * | 6/2002 | Criton et al. | 600/454 |
| 2003/0083578 A1 * | 5/2003 | Abe et al. | 600/447 |
| 2005/0119553 A1 * | 6/2005 | Pedrizzetti et al. | 600/410 |

FOREIGN PATENT DOCUMENTS

| | | |
|---|---|---|
| WO | 9949775 | 10/1999 |
| WO | WO 9949775 A2 * | 10/1999 |
| WO | 0245587 | 6/2002 |

OTHER PUBLICATIONS

Hein et al., "Current time-domain methods for assessing tissue motion by analysis from reflected ultrasound echoes—a review," Mar. 1993, IEEE, vol. 40, pp. 84-102.*

* cited by examiner

*Primary Examiner* — John Lee
(74) *Attorney, Agent, or Firm* — Woodland Emhardt Moriarty McNett & Henry LLP (57) ABSTRACT

A method of tracking position and velocity of objects' borders in two or three dimensional digital images, particularly in echographic images. A sequence is acquired of at least two consecutive ultrasound image frames of a moving tissue or a moving object. The frames are separated by a certain time interval. Reference points define a border of the moving tissue or object and the border is automatically tracked by estimating the position of the reference points in following image frames on the basis of the ultrasound image data of the acquired sequence of image frames.

8 Claims, 9 Drawing Sheets

METHOD OF TRACKING POSITION AND VELOCITY OF OBJECTS' BORDERS IN TWO OR THREE DIMENSIONAL DIGITAL IMAGES, PARTICULARLY IN ECHOGRAPHIC IMAGES

CROSS-REFERENCE TO RELATED APPLICATION

This application is a continuation of prior U.S. application Ser. No. 10/956,797, filed on Sep. 30, 2004, now U.S. Pat. No. 7,343,031 which claims the benefit of European Patent Application Serial No. 03425639.6 filed on Sep. 30, 2003, which are hereby incorporated by reference.

BACKGROUND OF THE INVENTION

The invention relates to a method of tracking position and velocity of objects' borders in two or three dimensional echographic images.

The automatic detection of borders and their rate of displacement is a fundamental topic in image analysis. The ability to automatically detect borders and their velocity allows easy recognition of objects, and an improved understanding of their function. In medical imaging the automatic recognition of an organ would eventually facilitate the extraction of objective measurements and automate some diagnostic processes.

A typical example is given by echocardiography in the imaging of the left ventricle. The possibility of an automatic detection of the endocardial border would give objective measurement of the ventricular volume. In particular, the extreme values (at proto-systole and tele-diastole) are commonly used for clinical diagnosis and the relative diagnostic index is calculated. In addition, the possibility to visualize the border velocities allows an easier assessment of the regional dynamical properties.

In general, and certainly in echographic imaging, the development of reliable methods for the automatic border detection is an extremely difficult task that has not received a generally reliable solution. In fact, in clinical practice, borders are drawn manually by the operator over the physiologically relevant frames of a sequence of images.

A strain rate analysis method in ultrasonic diagnostic imaging is disclosed in WO 02/45587. According to this document strain rate analysis is performed for ultrasonic images in which the spatial gradient of velocity is calculated in the direction of tissue motion. Strain rate is calculated for cardiac ultrasound images in the direction of motion which, for myocardial images, may be either in the plane of the myocardium or across the myocardium. Strain rate information is calculated for a sequence of images of a heart cycle and displayed for an automatically drawn border such as the endocardial border over the full heart cycle. The spatial gradient of velocity used for determining the strain and the displacements of the borders from one frame to a successive frame in a sequence of frames uses Doppler Tissue Imaging, or DTI. This technique allows the measurement of tissue velocity over all points in the ventricular wall. The measurement of velocity itself provides direct information about the wall motion and helps to uncover abnormalities not immediately observable from the visualization in B-mode imaging. The velocity measurement contains information about rigid body displacement, shear, and contraction/distension, the latter being immediately related to the myocardial activity. Post processing of the DTI velocity data allows the evaluation of additional quantities, namely strain-rate and strain, that are strictly related to the regional function. Segmental strain gives a direct evaluation of the degree of contractility of the myocardium during systole, as well as of its relaxation during ventricular filling.

Nevertheless, DTI suffers from a few drawbacks consisting in limitations of the technique. The evaluation of velocity, and to a greater degree, rate and strain, requires a higher frame rate with respect to B-mode imaging because velocity is a more rapidly varying function than B-mode displacement. A Doppler signal requires additional processing with respect to a simple echo.

Doppler tissue imaging suffers further of an intrinsic limitation due to the fact that only the component of velocity along a scanline can be measured. This limitation has several drawbacks. When tissue moves in a direction that is not aligned with the scanline, the Doppler velocity does not reflect the effective tissue kinematics. Only the component of strain and strain rate along the scanline can be evaluated correctly, giving a reduced view of the local deformation state. This limits the application of DTI to the anatomic sites that can be imagined aligned along a scanline. In echocardiography this corresponds essentially to the interventricular septum and to the lateral walls in apical view.

BRIEF SUMMARY

The present invention achieves the above mentioned aims with a method of tracking position and velocity of objects' borders in two or three dimensional digital images, particularly in echographic images, by acquiring a sequence of at least two consecutive ultrasound image frames of a moving tissue or a moving object, where the ultrasound image frames are separated by a certain time interval. A certain number of reference points of a border of a moving tissue or object at least on a first image frame of the sequence of image frames are defined. The border of the moving tissue or object in a following frame by is automatically determined by determining the new position of the reference points of the border in the following image frame of the sequence of image frames. This determination is done by estimating the position of the reference points in the following image frame of the sequence of image frames on the basis of the ultrasound image data of the acquired sequence of image frames. The sequence of image frames acquired is a sequence of consecutive B-mode, grey scale ultrasound images. On a first frame a border line is drawn either manually or by means of an automatic border detection algorithm. The border is defined by a trace of pixels of the image frame coinciding with the border line. The original trace of pixels coinciding with the manually or automatically drawn border line is followed in time by searching the maximum likelihood of the trace of pixels in the following image frame with the trace of pixels in the first or timely previous image frame of the sequence of image frames by analyzing the image pixels in the neighborhood of the said trace of pixels.

An object of the present invention is to provide a method for tracking position and velocity of objects' borders in two or three dimensional digital images, particularly in echographic images, which overcomes the drawbacks of the known tracking methods by reducing the load actually needed for acquiring the usable ultrasound image data, and for evaluating ultrasound imaging data in order to track the displacement of a border of a moving tissue or a moving object in a sequence of consecutive ultrasound image frames.

Another object of the present invention is to provide for a method which can lead to more reliable results in tracking the borders of a moving tissue or object on a sequence of consecutive ultrasound image frames.

DETAILED DESCRIPTION

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

The following is an overview of the disclosure. A more detailed description follows with reference to the Figures.

According to one embodiment of the present invention, the tracking of the border line is carried out by defining a certain number of reference points on the manually or automatically drawn border line on the first image frame and by using the method of the so called transmural cuts. The method of transmural cuts is disclosed in greater detail in the document PCT/IT02/00114 filed on 27 Feb. 2002.

More precise transmural cuts consist in defining a line which crosses the border line drawn and passing through one reference point. A physiologically appropriate direction can be chosen, which typically can be the orthogonal direction to the border line at the reference point. This operation is made for each image frame of the sequence of frames and for each reference point chosen. The pixels taken along each transmural line in each of the image frames of the sequence of image frames are placed in columns, with each column corresponding to one frame of the sequence of images. In this way the evolution along a transmural cut can be represented in a two-dimensional space time representation.

The above disclosed procedure is a reduction of a two dimensional problem applied to a two dimensional image, such as a B-mode ultrasound image, to a one dimensional problem as a M-mode image. The tracking of the border, i.e. of the trace of pixels, is carried out along the space-time image using a cross-correlation procedure of the pixel column in the space-time image corresponding to a first image frame with the pixel column in the space-time image corresponding to a successive image frame of the sequence of image frames.

This technique can be applied to any kind of images in which the geometry of the border line drawn does not require any kind of special reference points to be tracked a priori such as, for example, closed border lines as the border line of the cavity of a blood vessel in a cross-section image of the vessel. When the object imaged has particular starting and ending points of a border which has a relevance as particular reference points in the motion executed by the border-line of the object, for example in the case of the walls of the endoventricular cavity, then a preventive cycle must be carried out for optimally tracking the border-line of the object along the sequence of image frames.

According to a further embodiment of the above mentioned method, when the object has few very representative points the general topology of the border line of the object imaged can be represented by tracking the motion of these few representative points prior to carry out the tracking of at least one or some of the reference points lying on the manually or automatically drawn border-line in each frame of the sequence of image frames. These representative points can be for example the starting and ending points of the border line when this is an open one. The representative reference points of the border of an imaged object can be also suggested by the physiology when the imaged object is a particular tissue or organ, such as for example the left ventricle. Thus prior to carry out the tracking of some or all of the reference points chosen on the manually or automatically drawn border-line of the imaged object along the sequence of image frames the tracking of this few representative reference points is carried out.

The tracking of this few representative reference points is carried out in a identical way as the one disclosed above for the other reference points on the border-line drawn manually or automatically on the first frame by using the method of transmural cuts for constructing space-time images of each of the few representative reference points and determining the displacement of these points in each of the frames of the sequence of image frames by means of cross-correlation between each of the pixel columns with the successive pixel column corresponding to the pixels along the transmural cut across the same representative point in the different image frames of the sequence of image frames. The direction of the transmural cuts can be chosen as the orthogonal direction.

According to a further feature, after having determined the displacement of the few representative reference points on the border-line of the imaged object in some or in all of the frames of the sequence of image frames, the position and the displacement of the other reference points on the border-lines at each image frame of the sequence of image frames are obtained by rescaling the originally drawn border-line in the first image frame in such a way to obtain in each image frame corresponding to a successive instant a topologically equivalent border line geometry with respect to the original border line. Typically this results in a translation of all points along the original border line. This preliminary rescaling allows to keep the representative reference points always in the proper position in all frames of the sequence of image frames by rearranging the other reference points so that the representative reference points maintains the same meaning relatively to the object in all frames of the sequence of image frames.

In a preferred embodiment, a sequence of at least two consecutive ultrasound image frames of a moving tissue or a moving object are acquired in which the ultrasound image frames are timely separated by a certain time interval. A border line is traced over one single first frame either manually or with the help of an automatic border drawing algorithm. The position displacements of one or more representative reference points are tracked over the entire sequence of consecutive image frames. The border line drawn on the first image frame is rescaled at least for some of the following image frames of the sequence of image frames, according to the corresponding position tracked of the representative reference points. A certain number of further reference points are defined which are distributed along the border line on the first image frame and falling on the border line. The position of each point is tracked independently from the others along the sequence of image frames. The position of the representative reference points and of the other reference points are tracked for each point independently in each of the image frames of the sequence of image frames that define a transmural cut line consisting of a line which crosses the border line drawn and passing through the reference point. The pixels taken along each transmural cut line in each of the image frames of the sequence of image frames are placed in columns, with each column corresponding to one frame of the sequence of images for representing the evolution along a transmural cut line for all instants of time at once in a two-dimensional space time representation. The tracking of the border, i.e., of the trace of pixels, along each transmural cut line is carried out along the space-time image using a cross-correlation procedure of the pixel column in the space-time image corresponding to a first image frame with the pixel column in the space-time image corresponding to a successive image frame of the sequence of image frames.

According to another embodiment, in both cases disclosed above when images are poor with a low signal-to-noise ratio, the space-time representation along the transmural cuts can be built using a line for the transmural cut with a thickness larger than that of a single pixel and by extracting the average value across such a thickness.

The above mentioned method can be further developed for carrying out a surface border tracking three dimensional imaging by acquiring a sequence of three-dimensional ultrasound imaging data sets, each three-dimensional data set being acquired with a predetermined time interval from the previous one. At least a principal section plane of each three dimensional data set along one chosen direction is defined for obtaining a sequence of two dimensional image frames along the section plane. A border line of the object imaged is drawn either manually or automatically on the first two dimensional image frame of the sequence of two dimensional image frames taken along the said section plane. The previously described tracing step are repeated for the two dimensional sequence of image frames, for each three dimensional data set of the sequence of three dimensional datasets defining a pre-established number of further secondary section planes crossing the at least one, and preferably all, of the principal section planes, the said secondary section planes being spaced apart one from the other along a predetermined direction and dividing the object represented by each three dimensional data set of the sequence of three-dimensional data sets in slices, for each secondary section plane in the sequence of three dimensional data sets constructing the corresponding sequence of image frames relative to the said secondary section plane, and for each sequence of two dimensional image frames determining a guess border line in one single frame, by letting the border line passing across the intersection points with the principal section planes. The guess border line is tracked by detecting a new border by applying the previously described steps and by substituting the time coordinate with the spatial coordinate along the said guess border line by defining a certain number of transmural cuts on the single image of the sequence of images along the guess border line. The pixels along the transmural cuts are identified and placed along each transmural cuts side by side for constructing a two dimensional image where the horizontal axis indicates the spatial coordinate along the guess border line. Cross correlation between each of the consecutive pixel columns in the said two dimensional image is calculated, thus tracking the border line in one frame for each of the sequences of two dimensional image frames corresponding to each of the secondary section planes.

According to a further embodiment, one or more further principal section planes can be defined. In a preferred embodiment two orthogonal principal section planes are chosen for carrying out the above mentioned method steps, the crossing line of the two principal section planes defining a preferred direction of the planes. The direction can be chosen as suggested by the topological or functional feature of the object imaged.

Considering ultrasound images of a biological tissue or of an organ such as for example the heart the direction can be suggested by physiological reasons. For example this physiologically relevant direction can be chosen as the cut across a central vertical plane such as the ventricle axis.

In order to better define the share of secondary section planes cutting the principal section planes, the method according to the present invention comprises the steps of defining bounds or limits for a distance range within which the share of the said secondary section planes is defined.

Preferably a topological or physiological relevant direction is chosen, particularly the same direction defined for determining the principal section planes, along which direction bounds are determined for the ends of a distance range within which the share of secondary section planes at least transversal, particularly perpendicular to the said relevant direction is determined.

Still according to a further embodiment, when determining the first guess border line, this one is determined as a physiologically relevant line passing through the reliable points.

According to the present border tracking method the correct border is determined along a sequence of two dimensional or three dimensional ultrasound image data and the correct border for each image frame can be displayed overlaid on the displayed image frame as an highlighted line characterized by a color which is different from the grey-scale B-mode image displayed.

By means of the above tracking method of the border of two dimensional images or three dimensional images of an object, it is also possible to determine the border line velocity and thus the border velocity of the object imaged. Once the displacement of the border line is known along the sequence of two dimensional or three dimensional ultrasound image data sets and the time interval between each two consecutive sets of image data are known, the component(s) of velocity in the direction of the transmural cut(s) can be estimated for each reference point by means of a simple calculation. The complete velocity vector is determined by evaluation of the other component(s) of velocity, the total number of components being two for two-dimensional imaging and being three for three-dimensional imaging.

Each missing component of velocity can be evaluated once again with the method of transmural cuts, such that for each reference point, on each image frame of the sequence of image frames, a transmural cut consisting of a line which crosses the tracked point and is directed along the direction where the additional component of velocity must be evaluated, typically orthogonal to the direction previous employed for tracking the border, the pixels taken along each transmural cut line in each of the image frames of the sequence of image frames are placed in columns for all instants at once in a two-dimensional space time representation. The evaluation of the velocity component along the chosen direction is carried out along the space-time image using a cross-correlation procedure of the pixel column in the space-time image with the velocity being given by the ratio of the column-wise displacement of the correlation maximum and the time interval between the corresponding frames.

This method is identical of that employed for tracking the border with the difference that only the frame-by-frame displacement is required and the eventual time integration of said displacement to get the motion of the border is ignored. A different evaluation of the velocity vector can be obtained by applying two dimensional-correlation techniques or a specific optical flow technique particularly developed for ultrasound image data of moving objects. The velocity estimation method can be carried out in combination with the above disclosed method for tracking the border of the imaged moving object. The method is an adaptation of known method so called OPTICAL FLOW methods, like a known method called PIV that is used in fluid dynamics.

Thus in displaying the B-mode images the border tracked can be drawn as a line as disclosed above and the velocity vectors of the border taken at certain number of points of the border line are displayed as arrows having a different color as the border line and the direction of the velocity vector and a length corresponding to the modulus of the velocity vector in the image plane of the two dimensional image displayed.

By means of the method according to the present invention a different approach for tracking borders of a moving object in two and three dimensional ultrasound imaging is provided where the borders are not "detected", rather they are "tracked", i.e. followed in time, starting from one reliable existing instantaneous trace that is commonly, but not necessarily, manually drawn by the experienced operator over one single frame. Using this approach all the ambiguousness that is present in a pure detection approach is cleared, and the original trace is followed in time by searching the maximum likelihood over its neighborhood in the following frames. The tracking technique for each single point is approached using a method based on transmural cuts that is similar to that introduced in the document PCT/IT02/00114 filed on 27 Feb. 2002. Afterward the velocity on the tracked borders is estimated on the basis of the same maximum likelihood between two consecutive frames.

The automatic tracking method disclosed here allows the tracking of a border on a sequence of two-dimensional or three-dimensional images, and the evaluation of the velocity vector field on such borders. In principle, the border could be tracked on the basis of the velocity vector only; however, a tracking procedure is a result of the summation (time integration) of the estimated velocities and is prone to an error growth in presence of small incorrect estimates. This approach reduces the two- or three-dimensional tracking to a combination of one-dimensional tracking problems along the single topological relevant direction (typically the orthogonal to the border) that can be much better controlled and made accurate. On the other hand, the accurate tracking result is employed to improve the estimates of the velocity vector.

The result of this procedure is the automatic definition of the border displacement and velocity over all frames of a sequence of images, starting from the border traced on a single image. Eventually, the border information will be used to evaluated some geometric properties, like volume, area, or sizes, of the organ. The border kinematics (tracking+velocity) allows an estimate of global quantities (like volumes, lengths) as well as local phenomena (like rotations, strain) in a unique approach.

The method according to the present invention is firstly described with reference to a two dimensional case. A sequence of two dimensional B-mode image frames is acquired. The frames are acquired at predetermined time interval one from the other.

Consider a sequence of two-dimensional (2D) images; mathematically, this is a three-dimensional (3D) information that is 2D in space and 1D in time. Consider that the images contain one organ/object or part of it, that changes its position and shape in time, of which organ we want to trace the border kinematics at all instants.

Figure 1:
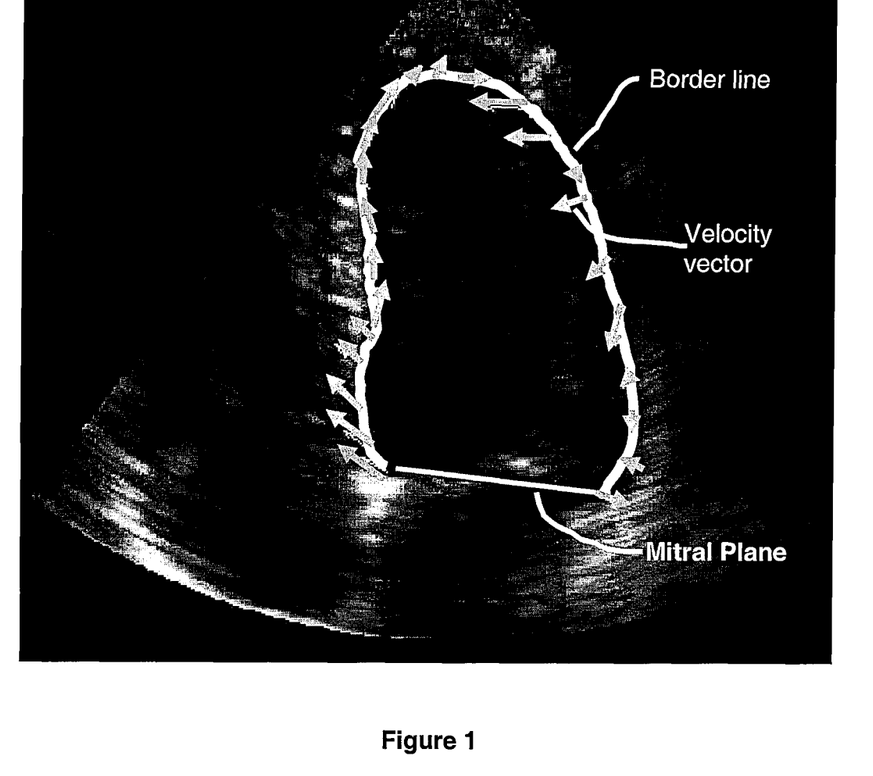
FIG. 1 illustrates an echographic image of the left ventricle, in long axis view (from the apex to the mitral plane), extracted from an echocardiographic recording (58 frames, 2 cycles) with an endocardial border (white) and the instant border velocity (white arrows).
Figure 2:
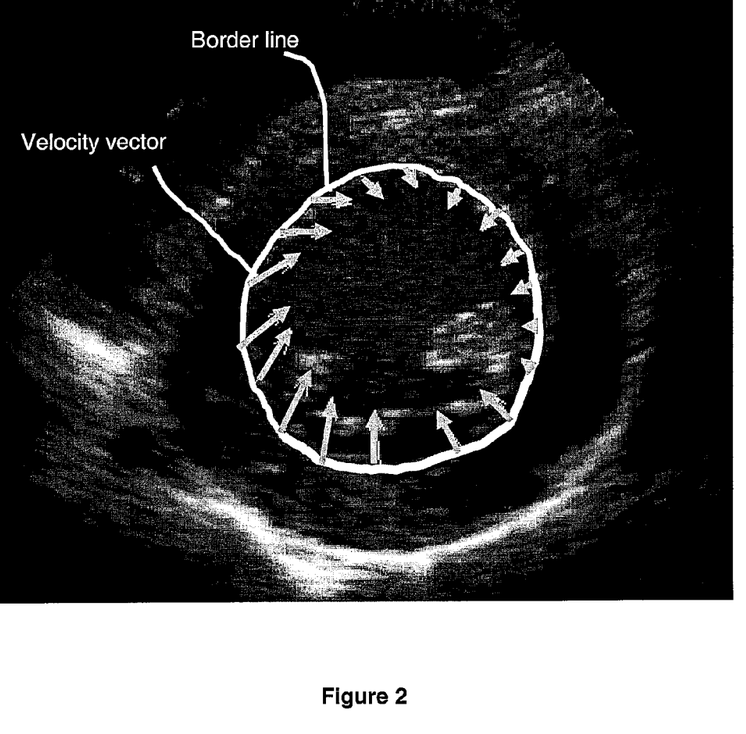
FIG. 2 illustrates an echographic image of the left ventricle, in short axis view (transversal section), extracted from an echocardiographic recording (49 frames, 2 cycles) with a "closed" endocardial border (white) and the instant border velocity (white arrows).

The method according to the present invention comprises a first step which consist of tracing the border over one single frame by defining a border line. A border is traced, manually or by another manual or automatic procedure, over one arbitrary frame. Such border is then defined as a sequence of N points, defined by their coordinate pairs (xi,yi) with i=1 ... N in the two dimensional image plane. The result of this step is illustrated in FIGS. 1 and 2. FIG. 1 illustrates an image of the left ventricle where the endocardial border points are traced from one side of the mitral annulus to the other side of the same mitral annulus. FIG. 2 illustrates an example in which the border is a closed one where the Nth point connects to the first one.

Referring now to a particular case like the one illustrated in FIG. 1, where the border has a staring and an ending point, the method according to the invention provides for a second step of tracking the most representative reference point of the border line drawn in the first image frame.

According to this step, the general topology of the object border is reproduced on all the images by tracking the motion of a few representative points. These are commonly the starting and final points of the border when this is an open one. In specific cases additional reference points can be added to improve the first evaluation of the region about which the border must be sought.

Figure 3:
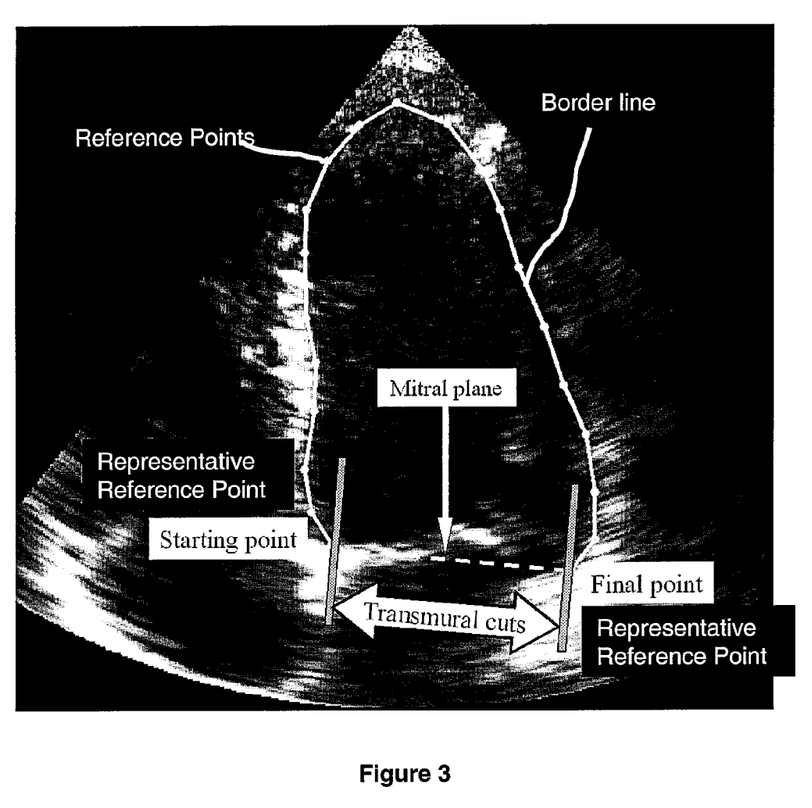
FIG. 3 illustrates an echographic image of the left ventricle, in long axis view, with the position of transmural cuts, passing from the edge points and normal to the transmitral plane, being indicated.

The displacement of the representative reference points along one or more specific directions is evaluated. FIG. 3 shows the reference points for a left ventricle (in long axis view) that are the starting and final points of the originally traced border. In this case, the physiology suggests to track the motion of these points in the direction instantaneously orthogonal to the mitral plane (that is defined by these points).

The tracking along a specified direction is performed by using the method of transmural cuts as follow. A line crossing the wall, passing through the point, and directed along the physiologically appropriate direction is drawn; in the case shown in FIG. 3 the appropriate direction is orthogonal to the mitral plane. In general two orthogonal direction can be employed. The pixels taken along the chosen direction line(s)

are placed in columns, each column corresponding to one frame of the sequence of images. In this way the evolution along a line can be represented for all instants at once in a two dimensional space-time representation (sometime referred as M-mode representation) where one axis is the distance along the line and the other axis is the time. An example of such a representation is shown in FIG. 4.

In the case of poor images with a low signal to noise ratio the space time representation can be built using a line for the transmural cut with a thickness larger than that of a single pixel and extracting the average value across such a thickness. The border tracking is then performed along the space-time image.

Tracking Along the 2D Space-Time Image

Figure 4:
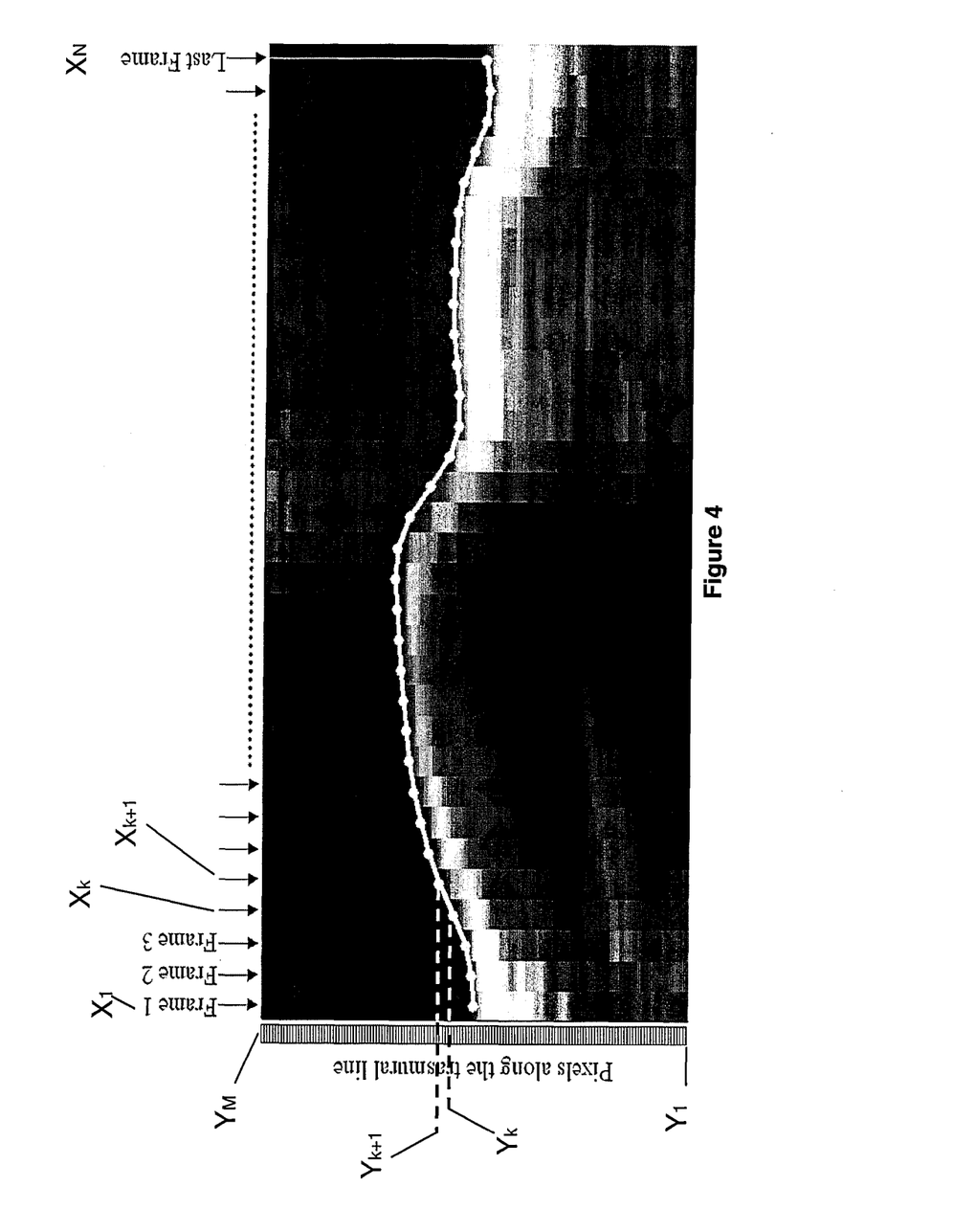
FIG. 4 illustrates a space-time representation, where space is along a transmural cut, of the echographic images sequence.

The tracking procedure is a procedure for following a border along one direction in a two-dimensional image like that in FIG. 4 starting from a known position at one instant.

Let us call x the horizontal direction and y the vertical direction, and indicate with xi, i=1 . . . N, where N is the number of columns in the image. The tracking is given by determination of a discrete sequence of real numbers yi=y (xi), starting from a known point yk corresponding to the columns xk.

This is a one dimensional tracking problem that can be solved with several possible standard methods. One method is reported here for giving completeness to the whole invention that can, however, employ also different techniques for this specific task when suggested by the specific imaging employed.

The displacement from the known point yk to the point yk+1 can be estimated by evaluating the cross-correlation between the entire column at xk with the entire column at xk+1. The cross-correlation function will present a maximum, the position of the maximum gives the value of the vertical displacement required to maximize the similarity between the two columns, therefore yk+1 is estimated by adding such a displacement to yk. This procedure is repeated between all pairs of nearby columns and the result is an estimate of the entire border yi, i=1 . . . N.

In this procedure it is convenient to employ windowing techniques that avoid side effects given by the two ends of the finite size columns. When applicable, it is also convenient to make use of the periodicity of the signal along x in order to perform the method in Fourier space.

The first estimate is improved by applying the same procedure recursively on increasingly reduced spatial width about the previously found border.

This first estimate yi can be further improved. To this aim a subset of the image is extracted by taking a few points above and below the first estimate yi, and a new image whose center corresponds to the sequence yi is generated. A snake procedure like the one described in Blake A., Yuille A. *Active Vision* MIT press, 1992., is employed to follow, in the new image, the image brightness level that passes through the fixed point yk. As a result the estimation of yi, i=1 . . . N is refined.

As it will become clear in the following description the tracking technique is a unique procedure that is common to different steps of the method according to the present invention.

As applied to the above mentioned step of the method according to the present invention, the result of this preliminary tracking procedure is the position and displacement, at all instants, of the most representative reference points along the predefined direction, or the vector combination when two directions are employed.

After this, all the other points of the original border are rescaled at each instant in order to get, at each instant a topologically equivalent border geometry. Typically, like in the example of FIG. 2, all the points are translated along the original curve.

This preliminary rescaling procedure permits to keep the reference points always at the proper position in all the frames, and to rearrange the other points so that the reference maintains the same meaning in all the frames.

The present step of tracking the most representative reference points such as the starting and ending point of a border line can be avoided when the specific geometry does not require or have any representative reference point to be tracked a priori. One example where this step can be avoided is given by the closed geometry in FIG. 2.

After having carried out the tracking of the most representative reference points if these points are present or in place of the said tracking step the method according to the invention provides for a further step consisting in the tracking of all the other reference point on the border line drawn manually or automatically in the first step on a first two dimensional image frame of the sequence of image frames.

Figure 5:
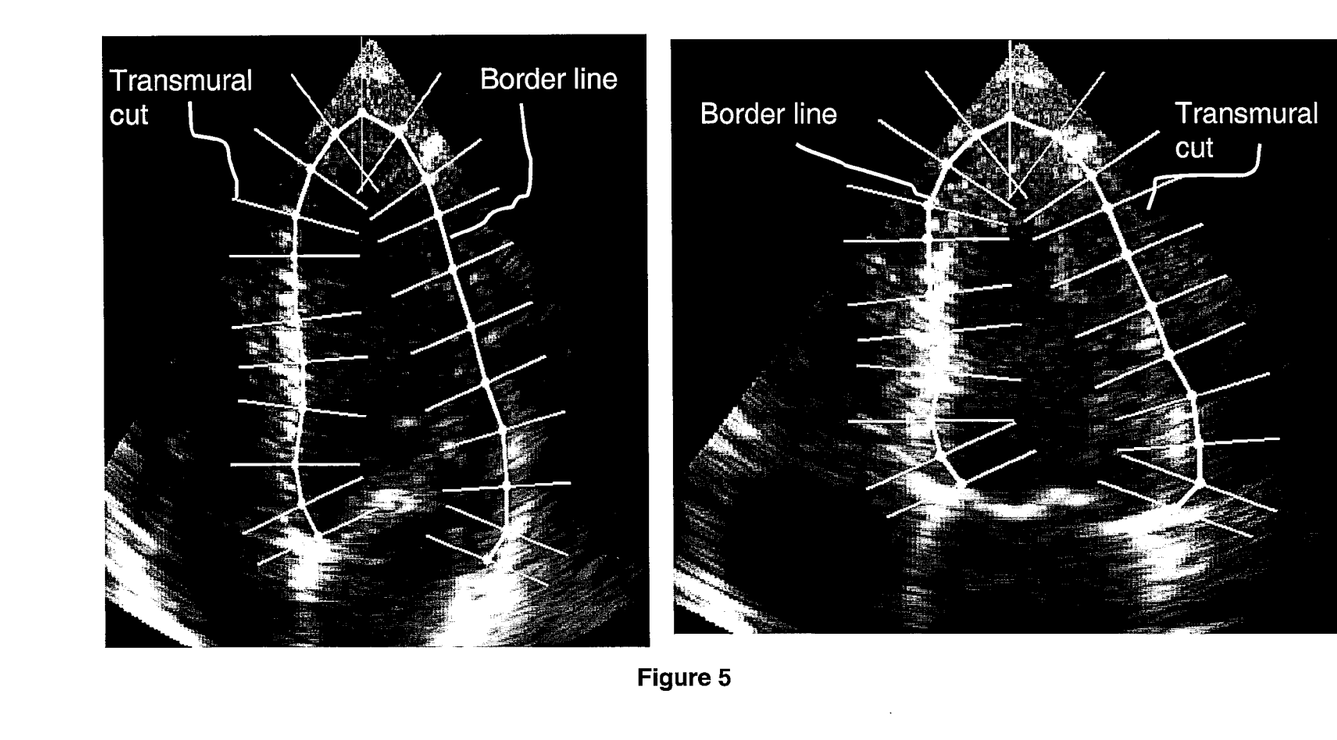
FIG. 5 illustrates an echographic image of the left ventricle, in long axis view, during diastole (left) and systole (right), showing a rescaled endocardial border and instantaneous transmural cuts on each of the original points.

For each point, independently, the tracking along a specified direction is performed by using the method of transmural cuts as follow. A line crossing the wall, passing through the point, and directed along the physiologically appropriate direction is drawn, this operation is made for each instant/frame of the sequence of image frames because the points are not fixed in time but they have been previously rescaled at each instant accordingly with the instantaneous displacement of the reference points. In most cases, like in the case shown in FIG. 5, the appropriate direction is taken at each instant as orthogonal to the rescaled border. The pixels taken along each transmural line are placed in columns, each column corresponding to one frame of the sequence of images. In this way the evolution along a transmural cut, that is not fixed in all frames time but is slightly modified accordingly to the rescaling, can be represented for all instants at once in a two-dimensional space time representation analogous to that shown in FIG. 4.

In the case of poor images with a low signal-to-noise ratio the space time representation can be built using a line for the transmural cut with a thickness larger than that of a single pixel and extracting the average value across such a thickness.

The border tracking is then performed along the space-time image using the same technique employed in the step of tracking the representative reference points and disclosed above in a detailed manner.

The result of this step is the position, at all instants, of all the points along the predefined direction, or the vector combination when two directions are employed. At this stage all the original points have been tracked in time, each one independently, and we have a new border tracked over all frames.

It can be useful, especially in poor quality images, to improve the estimate by including a spatial coherence in the tracked border. This can be done by verifying the likelihood of the tracking between neighboring points and correcting the eventual discrepancies with appropriate filters or validation methods.

As an additional procedure the method according to the present invention can be provided in combination with a procedure for determining the instant border line velocity vector for each one of the reference pints defined on the border line as tracked on each two dimensional frame.

For each point, independently, the velocity vector can be known when two direction (three for three-dimensional imaging) are employed for displacing it. When a single direction is employed, the complete velocity vector can be evaluated by selecting additional direction for the transmural cuts on the already displaced point and evaluating the velocity along the additional direction.

In the case of poor images with a low signal-to-noise ratio the space time representation can be built using a line for the transmural cut with a thickness larger than that of a single pixel and extracting the average value across such a thickness.

Alternatively, the complete velocity vector can be evaluated by a two-dimensional correlation technique or a specific optical flow technique adapted to the particular case of ultrasound imaging B-mode data. The two-dimensional result can then be improved by imposing its accordance with the previous estimate obtained for one component from the transmural cut approach. Results of the entire procedure are shown, for one frame, in FIGS. 1 and 2.

Three-Dimensional Imaging

The same steps described for the analysis of two-dimensional imaging can be employed for the border tracking in three-dimensional imaging. Such an extension is straightforward by using the previous steps in an appropriate combination, and substituting, in one case, the time direction with one spatial direction. Eventually no additional manual intervention is necessary with respect to what is done in two-dimensions, i.e. the indication of the border in one 2D frame.

A sequence of three-dimensional (3D) datasets is mathematically a four-dimensional (4D) information that is 3D in space and 1D in time. Consider that the images contain one organ/object or part of it, that changes its position and shape in time, of which organ it is desired to trace the border at all instants, the border now being a sequence of two-dimensional surfaces.

As a first step the method according to the present invention provides to choose one principal section plane which cuts to the three-dimensional dataset, and to apply the entire two-dimensional technique disclosed above on such plane.

The principal section plane of the 3D dataset is one plane, preferably along a physiologically relevant direction. Cutting the 3D datasets of the sequence of 3D datasets with this plane furnishes one sequence of 2D images.

Figure 6:
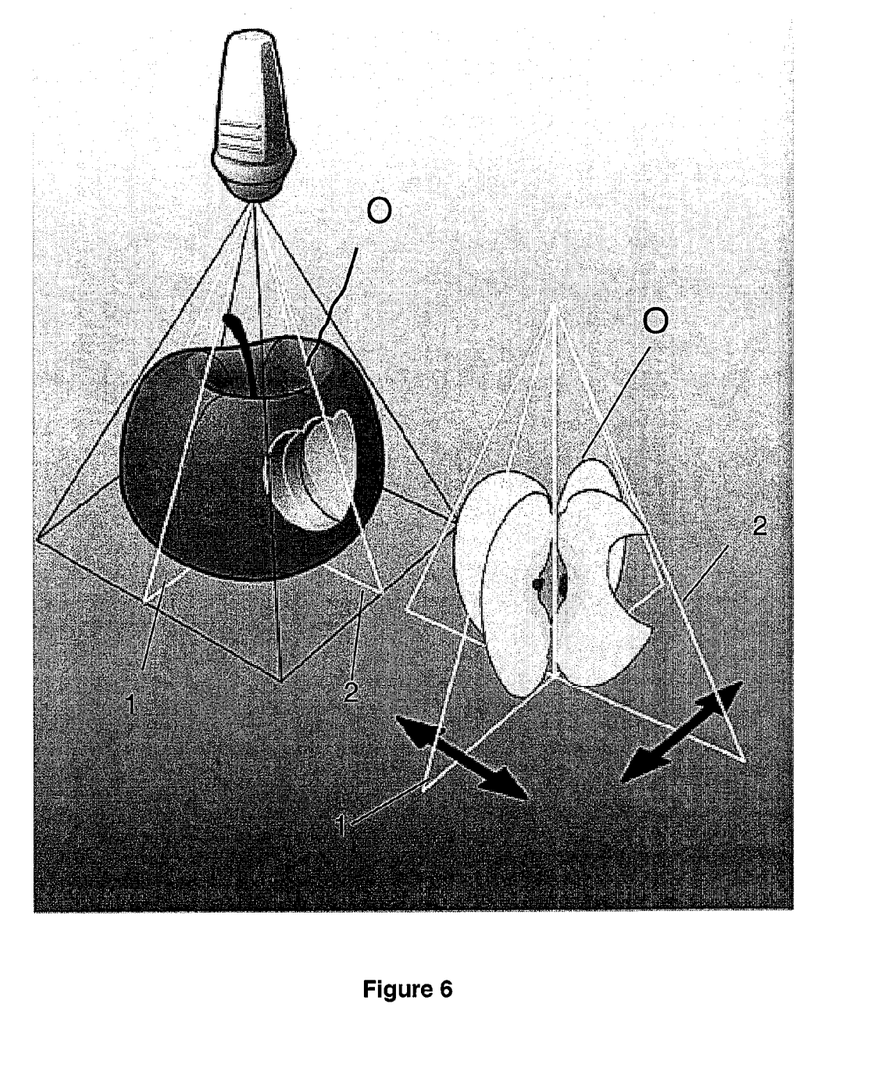
FIG. 6 illustrates a schematic view of an example of cutting a three-dimensional dataset with two orthogonal planes, having one common direction, to get two two-dimensional images.

FIG. 6 illustrates the cutting of a three-dimensional data set of ultrasound image data of the object 0 with two orthogonal principal section planes 1 and 2 oriented in the vertical direction.

For each principal section plane the entire tracking procedure as disclosed above for the sequence of two dimensional images is applied to this two-dimensional sequence of images taken on the principal section planes in order to track the border and evaluate the velocity on such principal section plane. This border is the signature of the sought border kinematics on the plane.

The above steps can be repeated with more than one or two principal section planes to improve the reliability of following steps in poor quality images.

After having carried out the above mentioned step a further step is carried out consisting in defining secondary section planes to the three-dimensional dataset, and applying the two-dimensional technique on single frames substituting the time direction with one spatial direction.

The previous step allows to define the bounds of the surface border. For this, one direction is chosen over the plane cut used in the previous step, preferably a physiologically relevant one (like the ventricle axis), and, for each instant, evaluate the upper and lower bounds along such direction of the border found in the previous step.

Figure 7:
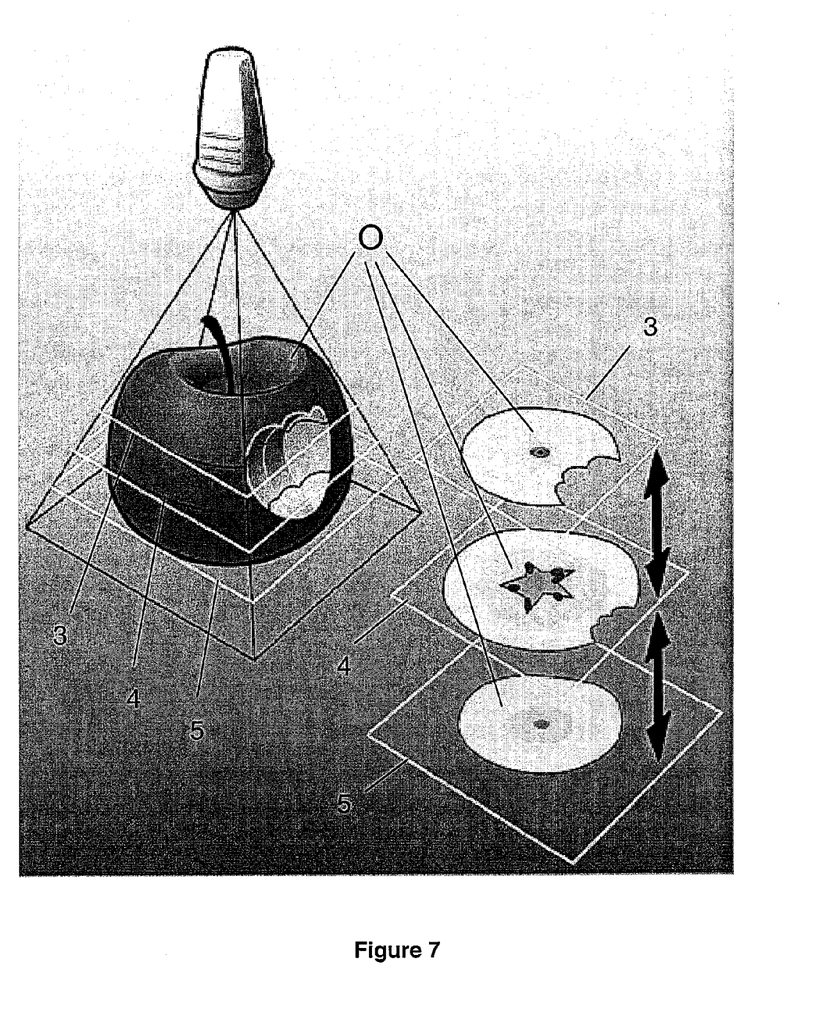
FIG. 7 illustrates a schematic view of an example of cutting a three-dimensional dataset with transversal planes that are orthogonal to the principal planes like those employed in FIG. 6.

The range between these limits, at each instant, is further divided in M internal points, and the 3D dataset is cut in correspondence of such M points, with M secondary section planes that are orthogonal to the chosen direction as indicated with 3, 4, 5 in FIG. 7. By means of the said secondary section planes the corresponding M sequences of 2D images are constructed.

Successively, for each sequence, a reliable border in one single frame is defined, commonly the same frame used when the borders are drawn manually during the previous step relative to the principal section planes.

Figure 8:
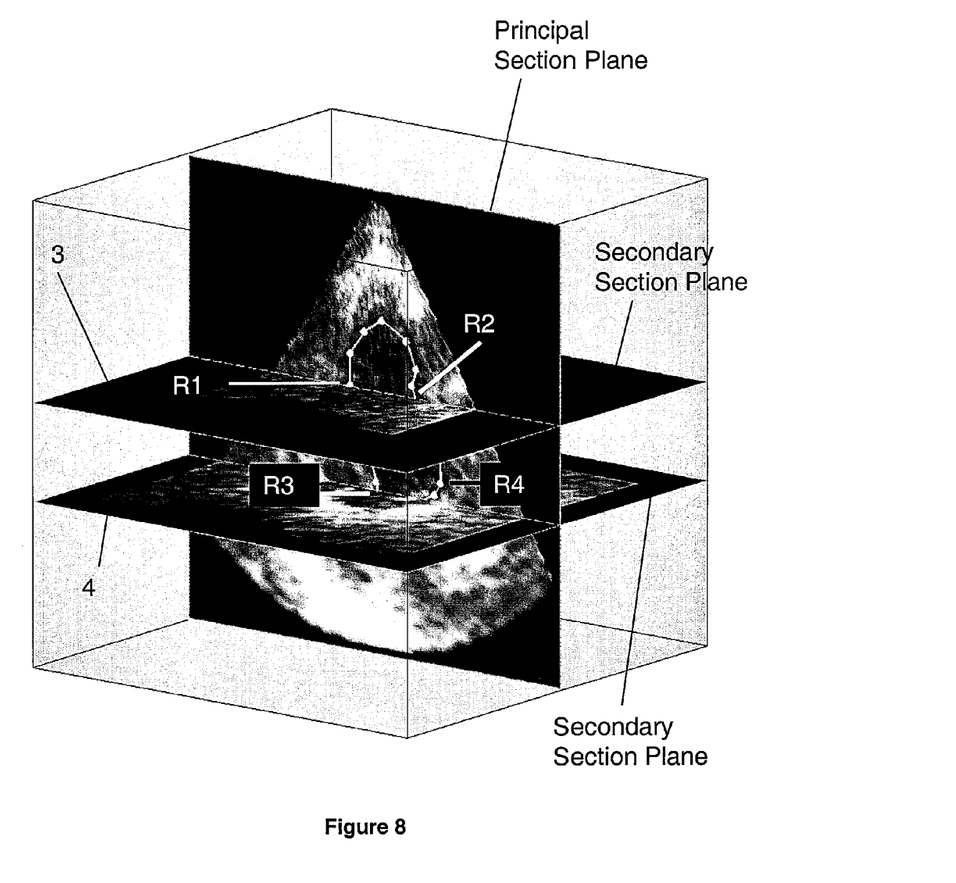
FIG. 8 illustrates slices on a three-dimensional echographic dataset of the left heart.
Figure 9:
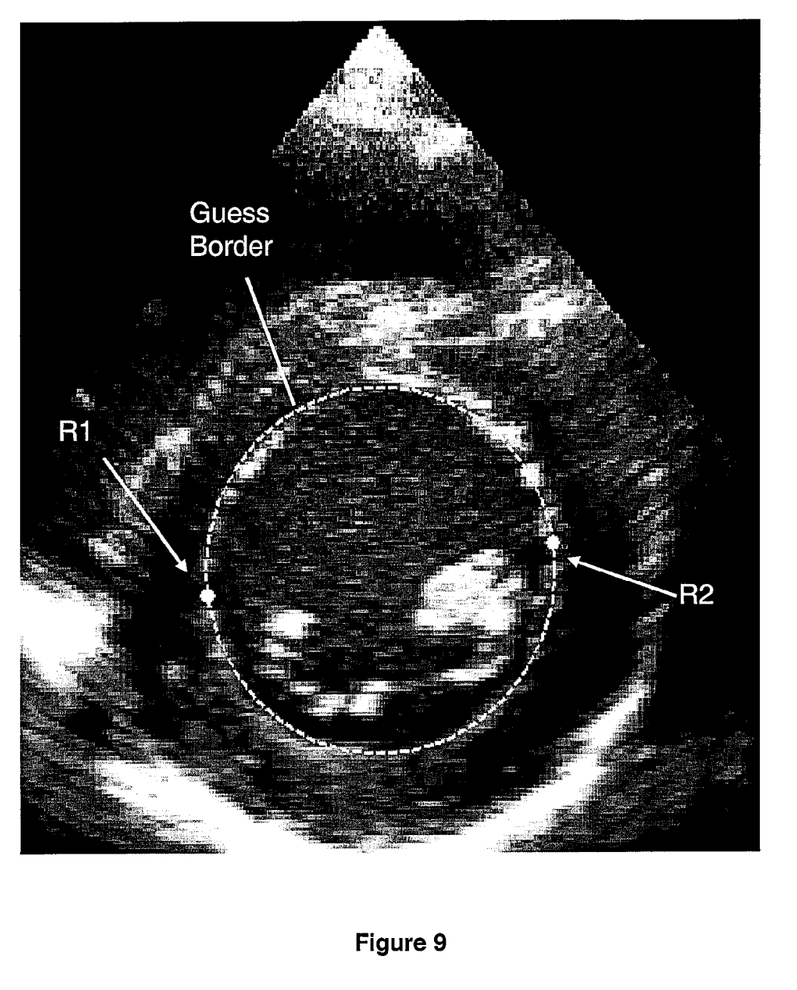
FIG. 9 illustrates a horizontal slice on a three-dimensional echographic dataset of the left heart, showing starting points and a circular first guess border.

In each of such single M frames, the border now contains one or more reliable points, at the intersection with the principal section plane or planes 1, 2 and that come from the border(s) determined in the previous step relative to the principal section planes as illustrated in FIG. 8 and indicated by R1, R2, R3, R4. A first guess border is constructed as a physiological relevant one passing through these reliable points R1, R2, R3, R4. An example of the said guess border on a secondary section plane is illustrated in the example of FIG. 9. Here the two dimensional image on a secondary section plane is illustrated together with the two reliable points R1 and R2. The guess border passing through the said two reliable points R1 and R2 is given by given by a circle in the transversal images of the left ventricle.

A new border is now detected by the same procedure used for a single transmural cut as disclosed in the previous chapter for the two dimensional case, this time however, substituting the time coordinate with the spatial coordinate along such first guess border as follows. Make a number of transmural cuts on the single image along the guess border, place the pixel found along each cut side by side in a new two-dimensional image and obtain a new image, like that in FIG. 4, where the horizontal axis does not indicate the time coordinate but the spatial coordinate along the tentative border. As a result the correct border is tracked in one frame for each of the M sequences.

The above mentioned procedure is applied on all the sequences obtained from the appropriate cutting of the three-dimensional dataset according to each secondary section plane defined. The tracking technique disclosed above in the previous chapter of the two dimensional ultrasound imaging is applied to each of the M sequences taking as a starting, reliable, border that found on one frame in the step relating to the secondary section planes. The resulting M borders will define the complete surface border.

Similarly to the two dimensional case discussed above also in the three-dimensional imaging case the instantaneous velocity vector for a certain number of predefined points on the border surface can be calculated by using the same technique disclosed of the two dimensional case. The two dimensional technique disclosed above is used here by substituting the two dimensional estimate with a three-dimensional estimate of velocity.

When the tracking procedure is insufficient to define the entire velocity vector, this is done by selecting additional direction for the transmural cuts on the already displaced point and evaluating the velocity along the additional direction.

Alternatively, this is done by using a three-dimensional correlation or optical flow technique, in place of the two-dimensional one for evaluating the three-dimensional velocity vector.

While the preferred embodiment of the invention has been illustrated and described in the drawings and foregoing description, the same is to be considered as illustrative and not restrictive in character, it being understood that all changes and modifications that come within the spirit of the invention are desired to be protected.

What is claimed is:

1. A method of tracking position and velocity of object's borders in two or three dimensional digital images, particularly in echographic images, comprising the following steps:

acquiring a sequence of at least two consecutive ultrasound image frames of a moving tissue or a moving object, said ultrasound image frames being timely separated by a certain time interval, wherein said sequence of image frames acquired is a sequence of consecutive B-mode, grey scale ultrasound images;

drawing either manually or by means of an automatic border detection algorithm on a first frame a border line of said moving tissue or moving object being defined by a trace of pixels of the image frame coinciding with said border line;

automatically or manually defining a plurality of reference points along said border line;

defining transmural cuts for each image frame of said sequence of frames and for each reference point chosen, said transmural cuts defining a line for each reference point which crosses said border line, wherein each one of said transmural cut lines passes through a corresponding one of said plurality of reference points and has a direction substantially orthogonal to said border line;

placing the pixels taken along each transmural line in each of said image frames of said sequence of image frames in columns, each column of pixels corresponding to the pixels along one of the transmural cuts of one frame of said sequence of images;

forming a two-dimensional space-time representation of the evolution of the position of each reference point along the corresponding transmural cut, where one axis is the distance along the transmural cut and the other axis is time;

tracking said border line for each reference point defined on said border line along the corresponding two-dimensional space-time image by using a cross-correlation procedure, wherein said cross-correlation procedure determines the vertical displacement required to maximize the similarity of the pixel column in the space-time image corresponding to image frame N=i with the pixel column in the space-time image corresponding to image frame N=i+1;

determining the velocity vector for each said reference point along said border line; and displaying said velocity vector for each said reference point along said border line.

2. A method according to claim 1, characterized in that objects imaged have at least one representative reference point of a border, further characterized in that the tracking of said reference points defined on said border line a preventive tracking cycle of only the representative reference points are carried out.

3. A method according to claim 2, characterized in that said tracking of said representative reference points is carried out by using the method of transmural cuts for constructing space-time images of each of said representative reference points and determining the displacement of said points by means of cross-correlation between each of said pixel columns with the successive pixel column corresponding to the pixels along said transmural cut across the same representative reference point in the different image frames of said sequence of image frames.

4. A method according to claim 3, characterized in that after having determined said displacement of said representative reference points on said border-line, the position and the displacement of said other reference points on said border-lines are obtained by rescaling said manually or automatically drawn border-line in said first image frame in such a way as to obtain in each image frame corresponding to a successive instant a topologically equivalent border line geometry with respect to said original border line and to keep said representative reference points always in the proper position in all frames of said sequence of image frames by rearranging said other reference points so that said representative reference points maintain the same position relative to said object in all frames of said sequence of image frames.

5. A method according to claim 1, characterized in that the correct border line tracked is displayed overlaid on the corresponding displayed image frame as a highlighted line and identified by a colour which is different from the grey-scale B-mode image displayed.

6. A method according to claim 1, characterized in that a first estimation of the instant velocity is determined for each reference point on said border line by dividing the displacement vector of each of said reference points from a first to a following image frame of said sequence of image frames by the time interval occurred between said first and said following image frames.

7. A method according to claim 6, characterized in that the instant velocity of said border line for each of said image frames of said sequence of image frames is determined for each of said reference points on said border-line by applying the method of transmural cuts along the additional direction required to evaluate the complete velocity vector.

8. A method according to claim 6, characterized in that the instant velocity of said border line on each of said image frames of said sequence of image frames is determined for each of said reference points on said border-line by applying two dimensional-correlation techniques or a specific optical flow technique adapted for ultrasound image data of moving objects.

* * * * *